United States Patent [19]
Schwartz

[11] Patent Number: 5,524,695
[45] Date of Patent: Jun. 11, 1996

[54] CAST BONE INGROWTH SURFACE

[75] Inventor: Melvin M. Schwartz, Point Pleasant, N.J.

[73] Assignee: Howmedica Inc., New York, N.Y.

[21] Appl. No.: 146,281

[22] Filed: Oct. 29, 1993

[51] Int. Cl.⁶ .................................. B22C 9/10; B22C 9/22
[52] U.S. Cl. .................................. 164/34; 164/45
[58] Field of Search ......................... 164/34, 35, 36, 164/45, 98, 29, 69.1, 115

[56] References Cited

U.S. PATENT DOCUMENTS

| | | | |
|---|---|---|---|
| 4,600,546 | 7/1986 | Grundei | 164/59 |
| 4,732,204 | 3/1988 | Tabardin | 164/35 |
| 5,016,702 | 5/1991 | Ahlers | 164/34 |

*Primary Examiner*—P. Austin Bradley
*Assistant Examiner*—Randolf S. Herrick
*Attorney, Agent, or Firm*—Peter C. Richardson; Lawrence C. Akers; Raymond W. Augustin

[57] ABSTRACT

An orthopaedic implant comprising a cast metal base member having an outer surface and an ingrowth surface comprising a plurality of attachment spacer elements of unequal lengths integrally cast with said base member and a metal attachment element integrally cast with said spacer elements, said attachment element having connecting elements extending between said spacer elements to allow attachment of the bone to occur between an underside of said connecting elements and the outer surface of said base member. The invention also consists of a method for preparing such an implant, wherein the spacer elements are of equal or unequal length, which comprises inserting a preformed ceramic pattern for the ingrowth surface into a die for the implant, injecting a meltable material in its molten state into the die at a temperature below the melting temperature of the ceramic to fill the holes and grooves of the pattern. The insert, partially encapsulated with the meltable material, is coated with additional ceramic material and the meltable material removed after melting to form a ceramic mold for the implant containing the ingrowth surface pattern. An alternative method for preparing a ceramic mold for the above-indicated orthopedic implant is to form the mold containing the ceramic insert by incrementally laying down the layers thereof under computer control.

17 Claims, 6 Drawing Sheets

CAST BONE INGROWTH SURFACE

BACKGROUND OF THE INVENTION

1. Field of the Invention

This invention relates to an integrally cast tissue ingrowth surface apparatus and a method for casting the same. More pariculary, the invention relates to an integrally cast bone or tissue ingrowth surface in a cast metal orthopedic prosthesis.

2. Description of the Prior Art

Investment casting or the "lost wax process" has been used for over 50 years in the production of medical and dental implants. The process derives its name from the investment of wax or other suitable mold material and ceramics used to produce an expendable mold for casting metallic implants.

The investment casting process used to process orthopedic implants is common to the industry and is used to produce implants from Co-Cr-Mo (Vitallium® [Pfizer Hospital Products Group, Inc., New York, N.Y.]) alloys as well as titanium alloys and stainless steels. Being well suited to the manufacture of the complex shapes typical of many implant designs, investment casting is used extensively to produce components for bone implants or total joint prostheses such as knees and hips.

These prostheses typically consist of metallic and polymeric components where the metallic components rest against bone on one side of the joint and bear against the polymeric component on the other. The bearing surfaces of a total joint have evolved in design to closely mimic the movement of the natural joint, while the bone contacting sides have evolved to assure improved fixation of the implanted prosthesis with the surrounding bone.

Until recently, total joint prostheses were designed for implantation with bone cement. For example, a polymethylmethacrylate (PMMA) grouting agent may be used to secure the prosthesis component against the surrounding bone. Implant surfaces contacting the cement were either cast smooth or with a two dimensional texture intended to improve fixation with the PMMA grout.

Recurrent loosening of these cemented implants, due to loss of support in underlying bone, lead to the development of prostheses with three dimensionally porous fixation surfaces which could be used without the PMMA bone cement. These prostheses, instead, rely on fixation via the ingrowth of bone or other connective tissue directly into the prosthesis surfaces, thereby anchoring the prosthesis to the bone.

These three dimensionally textured surfaces are created by bonding a suitable network of material, usually metal of the same composition as the implant, onto the implant's fixation surfaces to create a porous coating. The nature of the porosity present in the coating is generally a direct function of the materials and methods used to produce the coating.

Porous surfaces have been created by plasma spraying (U.S. Pat. No. 3,605,123) of fine metallic particles, or by sintering a loosely packed coating of metallic particles (U.S. Pat. No. 4,550,448, British Patent No. 1,316,809), or by diffusion bonding kinked fiber metal pads (U.S. Pat. No. 3,906,550), or overlapping mesh (U.S. Pat. No. 4,636,219).

In another concept, integrally formed ceramic filled porous areas are formed on the prosthesis. U.S. Pat. No. 4,722,870 discloses a method for investment casting a composite implant which produces a porous metal structure filled with a ceramic (hydroxyapatite). However, this structure cannot be accurately controlled nor can it be spaced a predetermined distance above the outer surface of the implant.

Other United States Patents describe mesh surfaces welded to the implant. Such a mesh is shown in U.S. Pat. No. 3,905,777 to Lacroix, U.S. Pat. No. 4,089,071 to Kalnberz et el., U.S. Pat. No. 4,261,063 to Blanquaert and U.S. Pat. No. 4,636,219 to Pratt et el. None of these surfaces are integrally cast with the prosthesis.

Each of the aforementioned methods for producing a porous ingrowth surface entails applying a porous network onto the surface of a metallic implant and bonding that network through the application of heat. Plasma spraying employs super heated gases to melt the metal particles to be sprayed. Sintering develops interparticle bonds in a porous coating by exposing the coating and implant metal to temperatures approaching their melting point, while diffusion bonding employs heat and pressure to promote atomic diffusion at the coating implant interface.

Each of these methods has its limitations. Plasma spraying cannot be adequately controlled to achieve a uniform interconnected pore structure in the coating. The temperatures required for sintering have a deleterious effect on the implant material's strength and diffusion bonding develops variations in pore structure and bond quality due to variations in pressure distribution during the coating process. Each of the processes is limited in its achievable pore size by the loss in coating strength which occurs as coating porosity increases.

Particulate porous coatings are also inherently accompanied by a dramatic increase in surface area of metal exposed to body fluids thereby increasing, proportionally, the corrosion products which are released after implantation.

European Patent Application No. 0 230 006 describes a bone implant with a netlike surface covering which contains a large number of perforations for the ingrowth of bony substance and consists of at least two assemblages of elongated crisscrossing elements. To provide satisfactory spaces with precisely predeterminable dimension for newly formed bone tissue, the elongated elements run parallel to the surface of the implant core that lies beneath them, with the attachment of the elements to the core material and maintenance of the distance from the core being ensured by projections.

Clinical reports exist of metal particles becoming loose from bonded coatings or fiber pads becoming detached on revision surgery. Furthermore, bonded coatings inherently develop stress concentrating surface notches at the coating- substrate interface which limit the locations a porous coating can be placed due to strength considerations. By their very nature, bonded coatings require the use of a secondary manufacturing process to affix the coating to the implant surfaces. These processes increase manufacturing costs through added labor, materials, tooling and fixturing.

U.S. Pat. No. 5,108,435 describes an orthopedic implant comprising a base and a porous surface wherein the base and surface are formed in a one-step casting process. The porous surface is uniformly spaced from the surface of the base.

SUMMARY OF THE INVENTION

This invention provides a one step process for creating porous surfaces on prostheses for purposes or improved implant fixation to the underlying bone, which is an integral part of the prosthesis, being produced by casting a three dimensional grid-like or lattice structure directly onto the prosthesis surfaces.

A further object is to provide a one step process for creating porous surfaces on prostheses which does not require thermal processing, which may be detrimental to the substrate materials mechanical properties, and does not involve the expense of a secondary coating process.

A further object is to allow an implant's porous surface to be precisely controlled relative to pore shape, pore size, pore size distribution, substrate bonding and coating stress concentrations.

It is another object of the invention to allow the pore sizes and shapes to vary and the spacing of the porous surface to be non-uniform.

These and related objects are achieved in the present invention by an apparatus having a cast metal base member having an outer surface designed to rest against a bone after implantation. A tissue ingrowth surface in the form of a cast porous metal lattice structure composed of grid-like cast elements spaced from the base member outer surface by cast spacer elements. The cast lattice is integrally cast with the base member, from the same metal, over at least a part of the outer surface thereof. The base member is solid and in the case of a tibial component, has a surface opposite the porous surface to support a meniscal bearing component. The metal utilized may be "Vitallium", titanium alloy or other suitable biocompatible metallic alloy.

An investment casting technique, wherein a meltable material is coated with a ceramic casting shell, may be utilized to cast the tissue ingrowth surface and the base member of the metal orthopedic implant. As is well known, the meltable material, such as wax, has a melting point lower than the ceramic material. A pattern for the porous surface is formed from the ceramic material, e.g., by injection molding, and inserted in the wax die corresponding to the implant. Wax is then added to the die partially encapsulating the ceramic pattern and forming a tri-axial matrix network. The combined wax-ceramic pattern is coated with a ceramic slurry to form a casting shell in the manner well known to the art. The meltable material is then removed from the casting shell by heating. As is well known, the empty casting shell is filled with molten metal and allowed to cool, thereby forming a one piece casting in the form of the pattern corresponding to the orthopedic implant with the lattice integrally cast therewith. Since the preformed ceramic pattern was designed to contact the shell formed by the ceramic slurry (ie., be semi-exposed) the process results in an implant having a three-dimensional porous fixation surface as an integral part of the cast orthopedic product. While wax is preferably used as the meltable material, other materials such as polystyrene may also be used. The depth of the grooves in the ceramic pattern and its thickness may be varied to obtain various spacings of the porous surface from the implant.

The process will enhance productivity by combining the wax injection operations of forming the implant component and porous fixation surface into one application. This will also eliminate any need for additional assembly or joining operations. The process will attain higher yields during the shell investment cycle of the casting process. Because the internal structure of the wax lattice network is embodied in the preformed ceramic, pattern designs are not restricted or inhibited by slurry viscosity or bridging of inadequate shell coating.

Alternatively, the wax injection and investment process may be avoided by preparing a mold comprising a ceramic shell and a hollow portion comprising a pattern for the metallic parts of the implant and a ceramic core comprising a pattern for the porous parts of the implant by the method of Direct Shell Production Casting™ (DSPC) (Soligen, Inc., Northridge, Calif.).

The DSPC method comprises forming a replica of the ceramic shell metallic implant and ceramic pattern for the porous sections of the implant on a computer. The mold is then formed by layers under the control of the computer. This is done by spreading ceramic powder in a printing-like process that is computer controlled. Once the first layer is dry, the next layer is put on, etc. The process forms a ceramic shell identical to that formed using a ceramic insert and wax as described herein by controlling where the ceramic is "printed" in each layer. After formation of the mold the process proceeds as described above with respect to the wax investment process after removal of the wax from the die ie., just prior to pouring metal into the ceramic mold in the "lost wax method".

These and other objects and features of the present invention will become apparent from the following detailed description considered in connection with the accompanying drawings, which disclose several embodiments of the invention. It is to be understood that the drawings are to be used for the purposes of illustration only, and not as a definition of the limits of the invention.

DETAILED DESCRIPTION OF THE INVENTION

Figure 3:
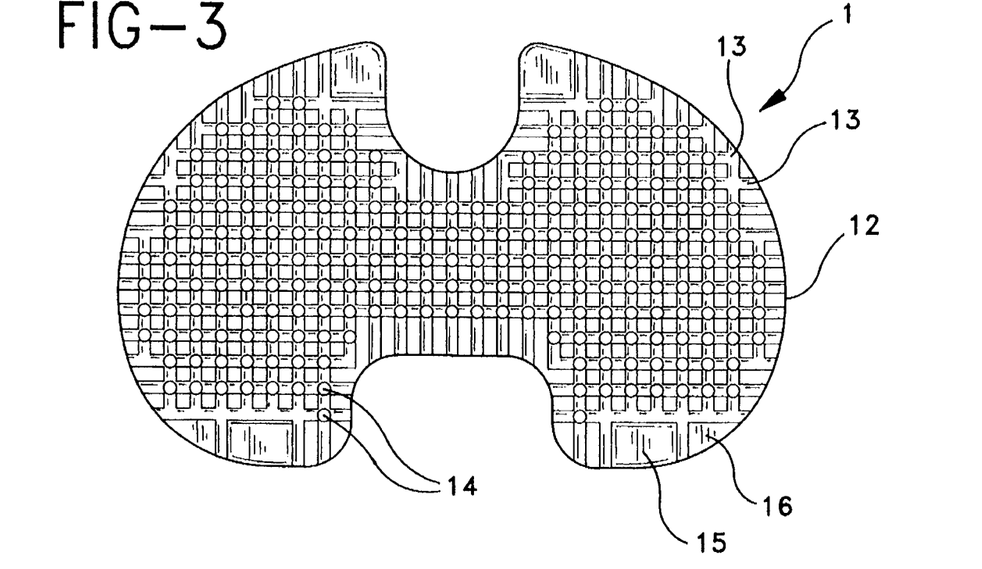
FIG. 3 is a bottom plan view of the ceramic insert of FIG. 2.
Figure 4:
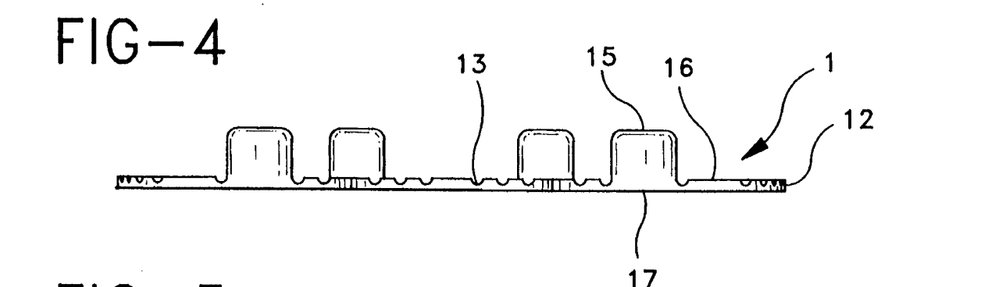
FIG. 4 is an elevational view of the ceramic insert of FIG. 2.
Figure 5:
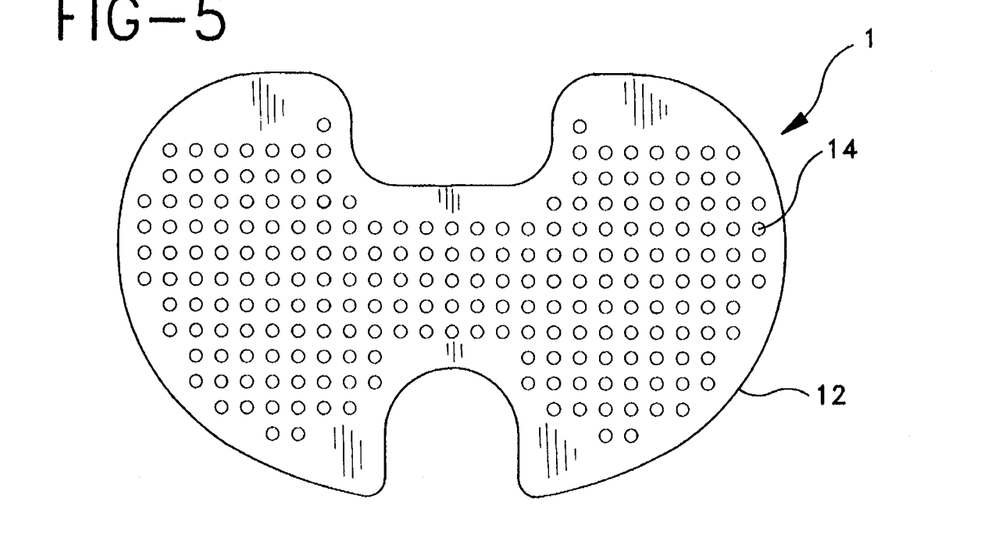
FIG. 5 is a top plan view of the ceramic insert of FIG. 2.
Figure 5A:
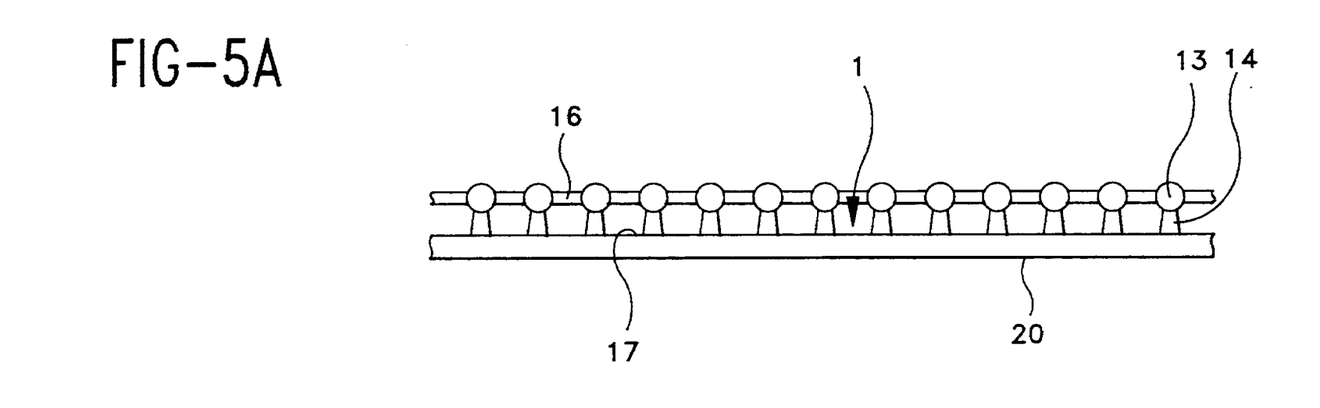
FIG. 5A is a crossectional view of the combined ceramic insert and wax pattern of the present invention.

Referring to FIGS. 3–5 there is shown a preformed ceramic core in the form of a ceramic insert for an ingrowth surface of an orthopedic implant, of the present invention, generally designated as 1. Core 1 may be in the form of a lattice element. Ceramic core 1 may be prepared by injection molding in any known manner. Core 1 is shown for use in manufacturing a knee tibial implant 2 such as shown in FIG.

Figure 1:
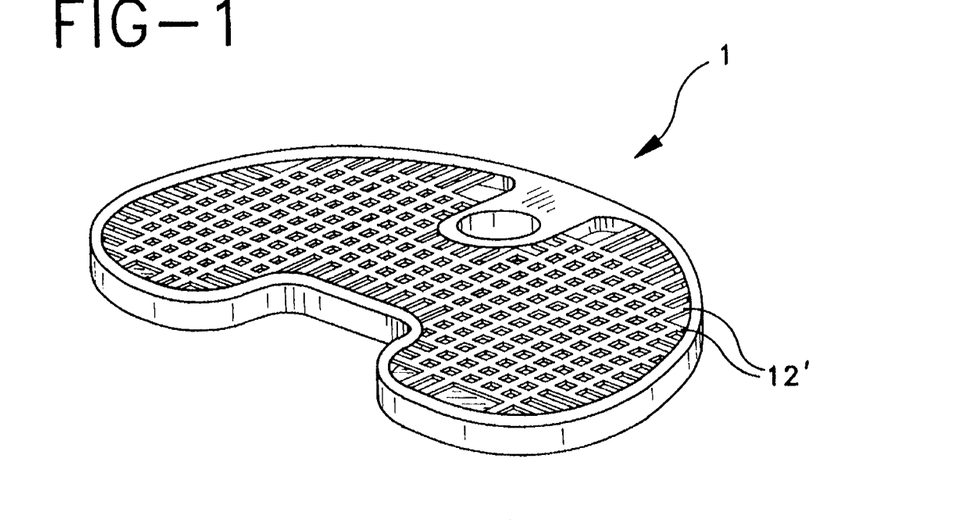
FIG. 1 is a perspective view of a cast tibial plate with the tissue ingrowth surface thereon.
Figure 2:
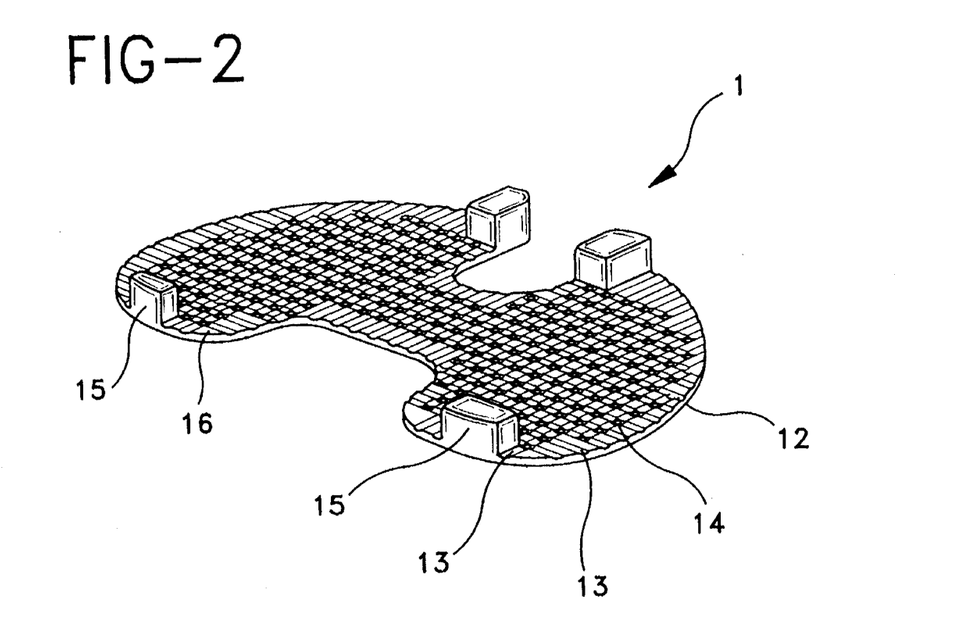
FIG. 2 is a perspective bottom view of a preformed ceramic insert for the porous surface of this invention.

1. The shape of the ceramic core may be changed to conform to the shape of implants for other indications such as hip or femoral knee components.

Ceramic core 1 consists of a flat ceramic sheet 12 comprising generally perpendicular grooves 13, in one surface 16 of said sheet, intersecting at holes 14. In addition, the core comprises projections 15 perpendicular to surface 16. Surface 17 of core 1 is generally flat.

A wax, or plastic, core for the implant may be produced by injection molding in any known manner such as by injection into a metal die (not shown) to form the implant shape in wax. The ingrowth surface pattern 1 is inserted into the component's implant wax pattern die with the surface 16 in contact with a corresponding lattice surface formed on the implant pattern die. Thus the cross member 12' of FIG. 8A corresponds to the shape of the wax filling the combined shape of the semicircular groove 13 on pattern 1 and a similar semi circular groove in the die (not shown). Wax is injected through holes 14 in ceramic insert 1 during the injection molding process to fill the grooves and holes of the ceramic core 1 to form a unitary implant pattern. After filling of the grooves and holes with wax the investment process proceeds with the combined core and wax pattern being coated with a slurry of colloidal silica binder of the type including refractory powders of zirconia, alumina and silica. The first coat of the slurry used to form the shell in the investment casting process is critical. A preferred slurry for this first coat is a colloidal silica binder (such as Du Pont's 30% colloidal binder) base with refractory zirconia and silica flours. The viscosity can be varied by adding more or less binder. The dip pattern must be designed to make sure that the one-piece pattern is completely and evenly coated. The pattern must be vibrated while draining, with air lightly blown over the lattice pattern to break up any air bubbles which might prevent the slurry from bridging the grid openings. With care, it has been found that this technique can be used to produce grid openings of about 50 mm (0.02 inches) and above. With the use of the injection molding process for the meltable material, various pattern shapes, such as square, rectangular or triangular, may be used for the tissue ingrowth surface. With this process, furthermore, the shapes and sizes can be accurately controlled. Thus, various pattern shapes can be fabricated to fit specific implant designs. Furthermore, the potential variability of pore spacing would allow for the use of bone inductive coatings or fillers such as hydroxyapatite to facilitate tissue or bone ingrowth as well as more precise engineering and control of pore structures as required for improved osseo integration or vascularization.

Figure 6:
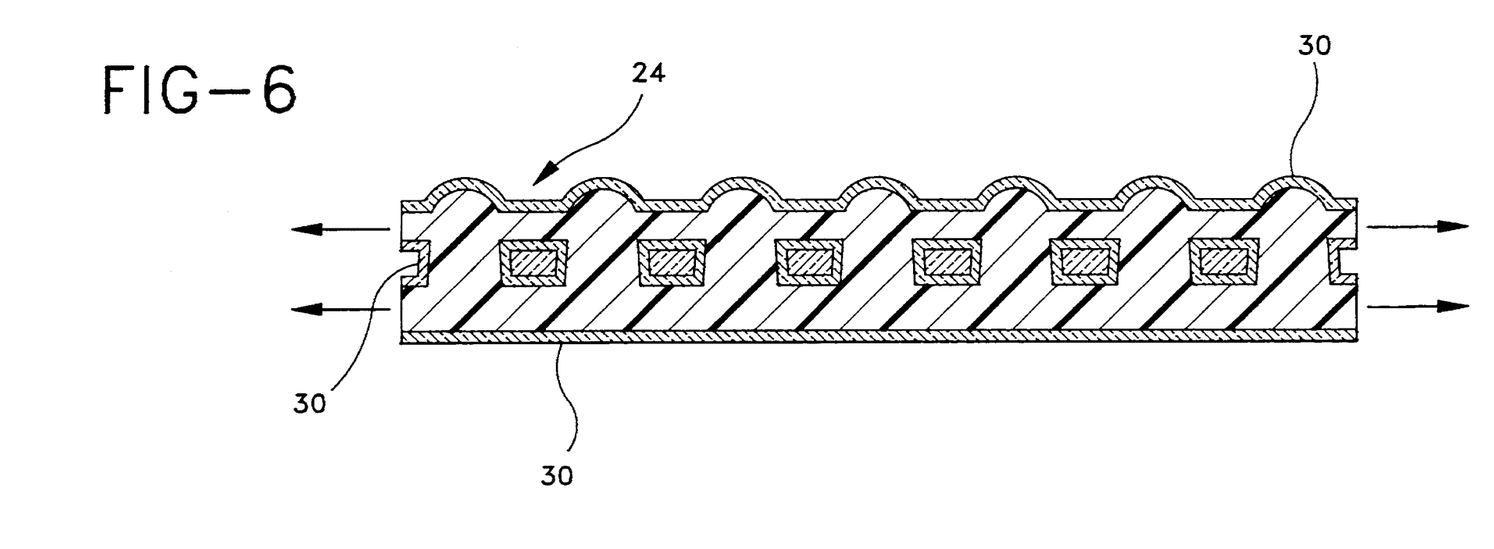
FIG. 6 is an enlarged cross-sectional view of the joined ceramic insert and the wax pattern covered by a casting shell.
Figure 7:
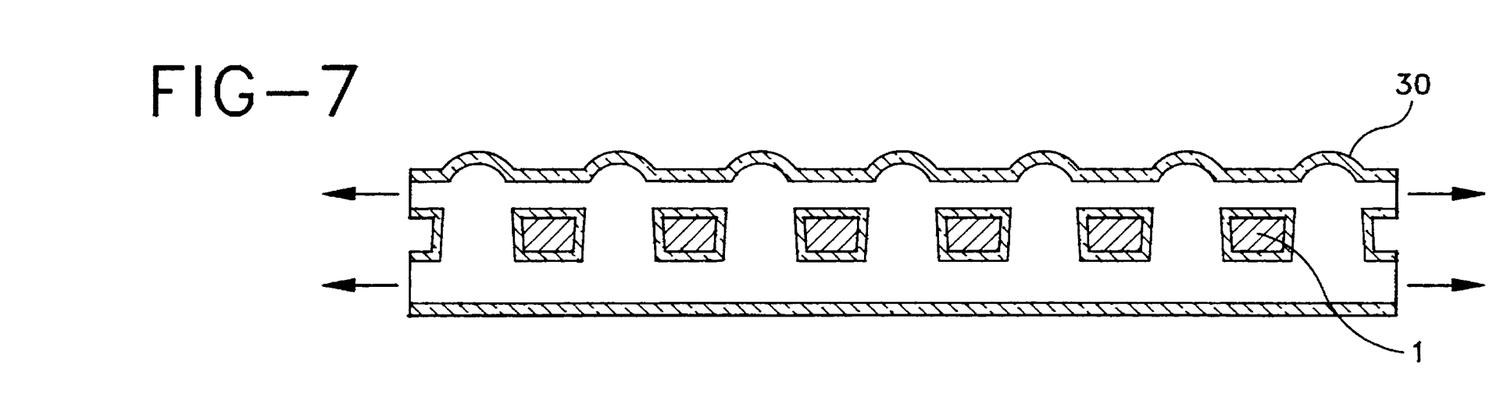
FIG. 7 is a view of FIG. 6 after removal of the meltable material by heating or after formation by the DSPC method.
Figure 8:
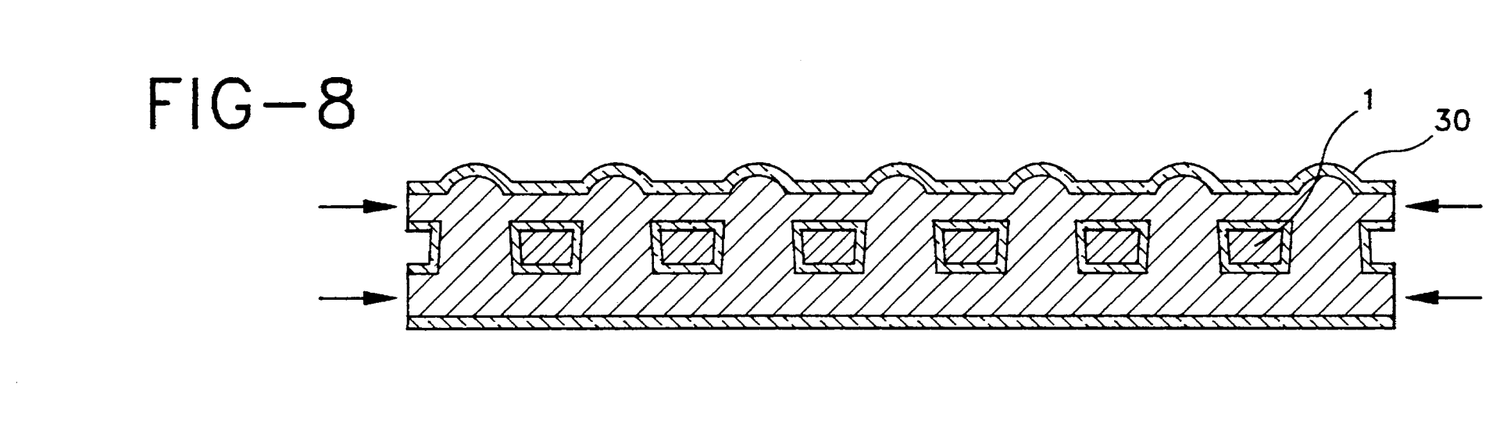
FIG. 8 is a view of FIG. 7 after molten base metal has been introduced into the casting shell of FIG. 7.

After the initial coat is allowed to dry, the process continues with, additional slurry coats being applied in the well known manner forming the ceramic shell 30 as shown in FIG. 6. The meltable part (ie., wax) of the combined pattern 24 made of the meltable material and the ceramic pattern 1 is then removed from the shell by heating in a well known manner. This results in a void being formed within ceramic shell 30 as shown in FIG. 7. A molten metal, such as Vitallium or a tantalum alloy or titanium, is introduced into the void, as shown in FIG. 8, and allowed to cool. Of course, it is well known that in order to cast titanium, special foundry practices must be followed. Under those circumstances, cast ingrowth surface of the present invention, comprising titanium, can be produced.

Figure 8A:
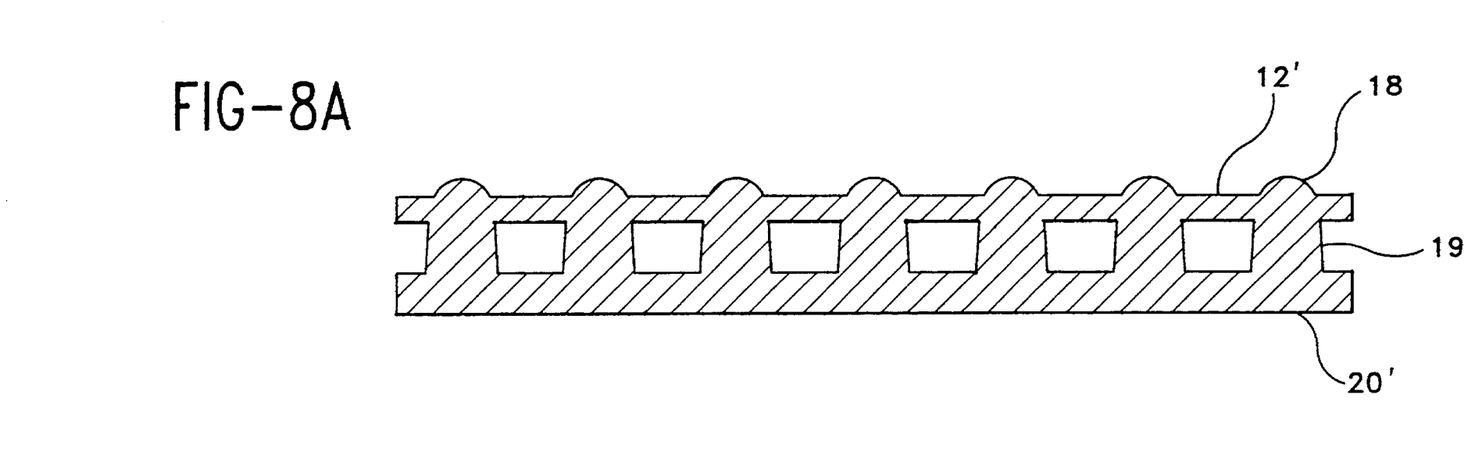
FIG. 8A is a cross-sectional view of the integrally cast orthopedic implant and lattice element of the present invention.

After removal of shell 30 and ceramic core 1, the integral one-piece casting is shown in cross-section, in FIG. 8A. The ceramic core 1 may be removed from the metal implant by treatment with a base. As can be seen, connecting elements 12' forming the lattice, the protrusion, 18, a spacer element 19, and the orthopedic implant base member 20 having upper surface 21 are now a one-piece casting of, for example, Vitallium or titanium.

Figure 9:
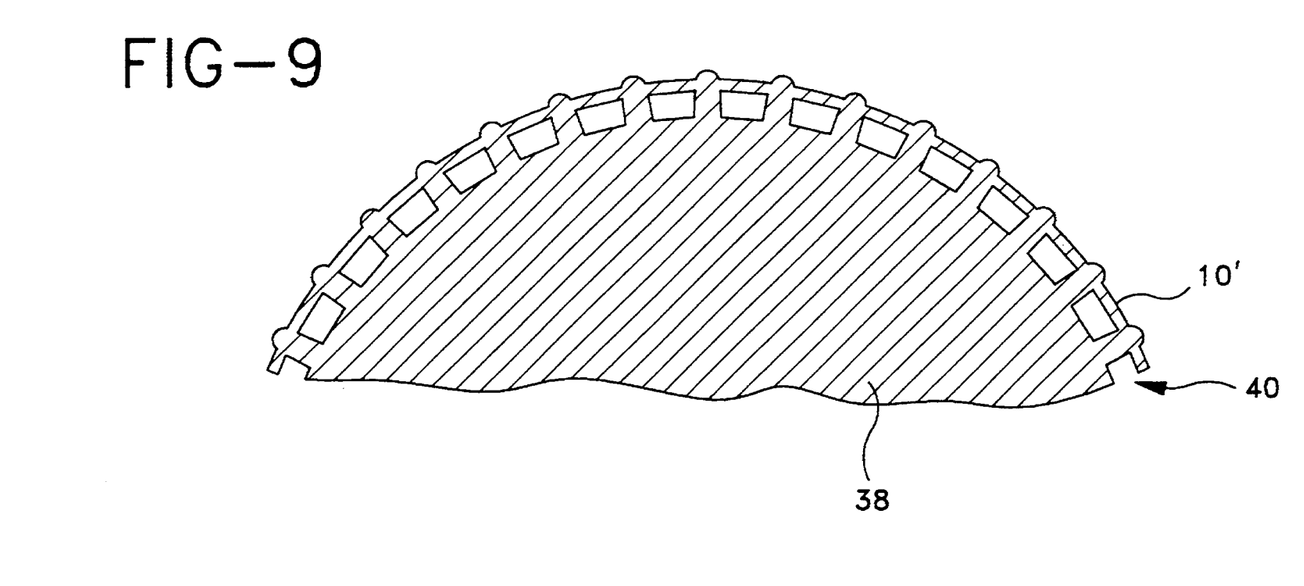
FIG. 9 is a partial cross-sectional view of a femoral component of a total hip prosthesis having the tissue ingrowth surface in the form of the lattice element integrally cast on the outer surface thereof.

Referring to FIG. 9, it can be seen that the integral cast lattice element 10' forming a tissue ingrowth surface can be easily produced on the outside of a femoral component of a hip prosthesis. This is accomplished by producing a spherical preformed ceramic-core that replicates the outer surface 40 of the hip prosthesis 38. utilizing a formulation of wax or polystyrene which is suitably flexible and can be wrapped around the outer surface 40 of the hip prosthesis 38. Such a wax is Yates JW-2® (Yates Manufacturing Co., Chicago, Ill. 60608) wax.

Figure 10:
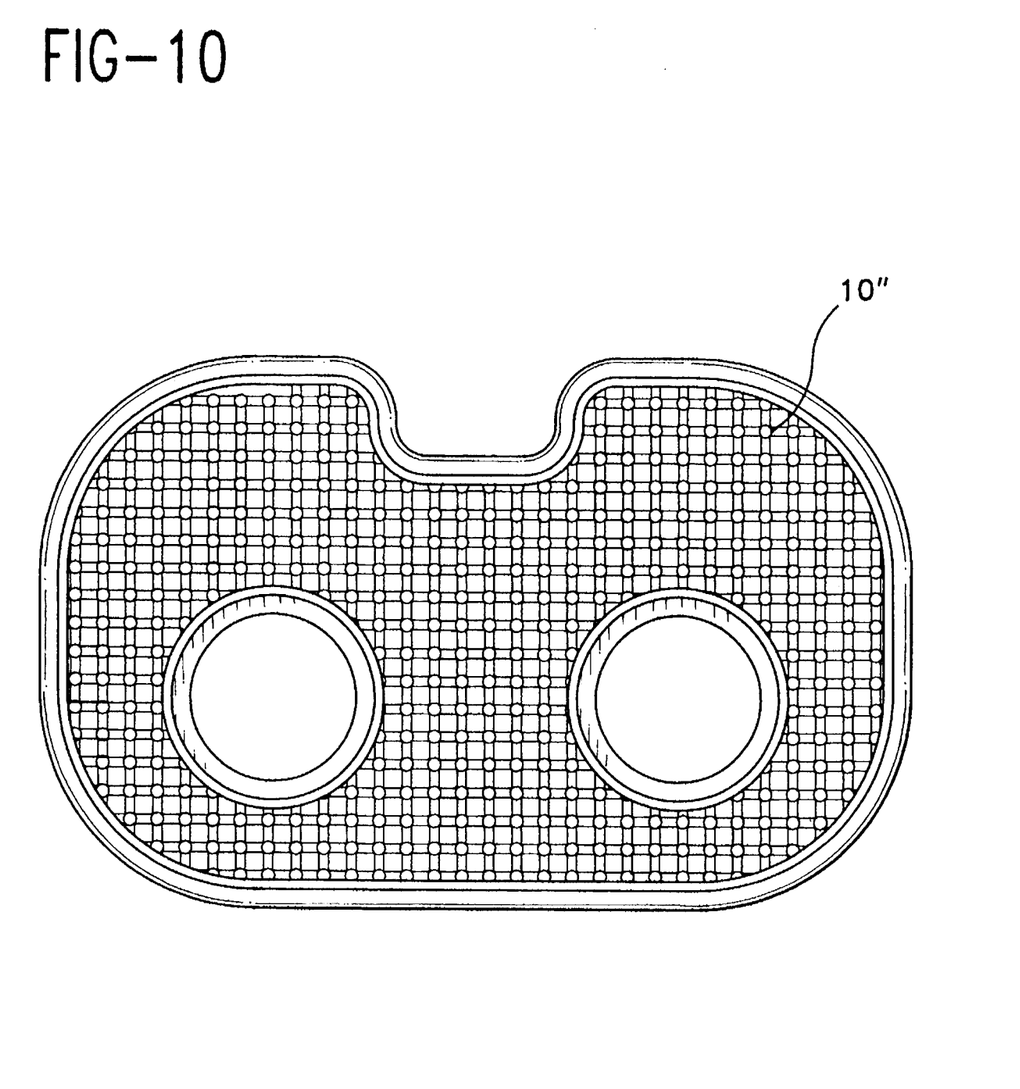
FIG. 10 is a plan view of a tibial plate having the ingrowth surface formed by the method of the present invention.

Referring to FIG. 1, there is shown a tibial component 2 of a knee prosthesis in which an outer surface is shown which is the bottom surface of the tibial plate (the surface which comes in contact with the top surface of the tibia after implantation) includes the porous surface thereby forming an ideal tissue ingrowth surface. FIG. 10 shows a plan view of a similar tibial component including lattice 10".

Alternatively, the mold of FIG. 7 may be prepared by the process of Direct Shell Production Casting™ (Soligen, Inc., Northridge, Calif.)

While several examples of the present invention have been described, it is obvious that many changes and modifications may be made thereunto, without departing from the spirit and scope of the invention.

I claim:

1. A process for preparing an orthopedic metal implant formed from a cast metal base member having a plurality of attachment spacer elements integrally cast with said base member extending outwardly from said outer surface, and a lattice element having connecting elements for contract with a bone extending between said spacer elements forming the porous portion to allow attachment to bone to occur between an underside of said connecting elements and said outer surface of said base member which process comprises the steps of:

forming a ceramic insert, said insert having grooves in a top surface of said ceramic insert and having through holes at intersections of said grooves;

forming a one piece structure by surrounding said ceramic insert with a material, meltable below the melting temperature of the ceramic, in its molten state and cooling the combination to form the one piece structure;

coating said one piece structure with a ceramic coating;

heating the coated structure and removing the meltable material to form the ceramic shell containing the hollow portion and the ceramic insert;

pouring the molten metal into a ceramic mold comprising a ceramic shell, said ceramic shell having a hollow portion for forming the base member, spacer elements and connecting elements of the implant;

said ceramic insert within said hollow portion of said ceramic shell forming the pattern for the porous portions of the implant; and removing the ceramic shell and excess metal, and removing the ceramic insert.

2. The process as set forth in claim 1 wherein said metal is a cobalt-chrome alloy.

3. The process as set forth in claim 1 wherein said connecting elements define openings between the outer surface of the cast metal base member to allow for tissue ingrowth.

4. The process as set forth in claim 1 wherein said connecting elements define openings between the outer surface of the cast metal base member to allow for the introduction of bone cement.

5. The process as set forth in claim 1 wherein said metal lattice element is in the form of a grid-like mesh comprised of a multiplicity of cross-members.

6. The process of claim 1 wherein said porous surface ceramic insert is removed from the implant by treatment with a base.

7. The process of claim 1 wherein said ceramic insert comprises a ceramic material selected from fused silica and alumina.

8. The process of claim 7 wherein said ceramic material is fused silica.

9. The process of claim 1 wherein said meltable material is a wax or thermoplastic polymer.

10. The process of claim 9 wherein said meltable material is a wax.

11. The process of claim 9 wherein said meltable material is polystyrene.

12. The process of claim 1 wherein said metal is selected from Vitallium, titanium, tantalum and alloys thereof.

13. The process of claim 12 wherein said metal is tantalum or an alloy thereof.

14. The process of claim 13 wherein said metal is Vitallium.

15. The process of claim 14 wherein said metal is titanium or an alloy thereof.

16. A process for preparing an orthopedic metal implant having a porous bone ingrowth portion formed on an outer surface thereof comprising:

forming a ceramic insert, said insert having grooves in a top surface of said ceramic insert and having through holes at intersections of said grooves;

molding a fugitive material around said ceramic insert to form a one piece structure; forming a ceramic shell around said one piece structure;

removing said fugitive material to form a cavity in said ceramic shell, a portion of said cavity is formed between a bottom surface of said ceramic insert and said shell for a cast metal base member, said holes in said ceramic insert for integrally casting spacer elements to said base member, said grooves in said ceramic insert and corresponding grooves formed in said shell for casting a lattice element having connection elements joining said spacer elements, said spacer elements forming the porous portions to allow attachment of bone to occur between an underside of said connection elements and said outer surface of said base member;

pouring molten metal into a ceramic mold comprising said ceramic shell, said ceramic insert and said cavity; and removing the ceramic shell, said ceramic insert and any excess metal.

17. A process for preparing an orthopedic metal implant having a porous bone ingrowth portion formed from a cast metal base member having a plurality of attachment spacer elements integrally cast with said base member extending outwardly from said outer surface, and a lattice element having connecting elements for contract with a bone extending between said spacer elements forming the porous portion to allow attachment to bone to occur between an underside of said connecting elements and said outer surface of said base member which process comprises the steps of:

creating a ceramic mold design comprising a ceramic shell and a ceramic core forming the porous portion for the metal implant on a computer;

converting the design into a mold having a ceramic shell with a ceramic core having intersecting grooves in a top surface of said core and having through holes at the intersections of said grooves, said through holes connecting hollow portions of said shell forming the implant base member to said grooves to form the lattice element, said mold formed under computer control, one layer at a time by spreading ceramic powder, then printing it with a liquid binder which hardens the powder;

pouring molten metal into the ceramic shell to form the implant; and removing the ceramic shell and excess metal.

* * * * *